US00PP34112P2

(12) United States Plant Patent
Bean et al.

(10) Patent No.: US PP34,112 P2
(45) Date of Patent: Apr. 5, 2022

(54) ***PLECTRANTHUS* PLANT NAMED 'WHITE001'**

(50) Latin Name: ***Plectranthus* hybrid**
Varietal Denomination: White001

(71) Applicant: Charles Andrew de Wet, Johannesburg (ZA)

(72) Inventors: Quinton Bean, Johannesburg (ZA); Charles Andrew de Wet, Johannesburg (ZA)

(73) Assignee: Charles Andrew de Wet, Johannesburg (ZA)

( * ) Notice: Subject to any disclaimer, the term of this patent is extended or adjusted under 35 U.S.C. 154(b) by 0 days.

(21) Appl. No.: 17/243,685

(22) Filed: Apr. 29, 2021

(51) Int. Cl.
*A01H 5/02* (2018.01)
*A01H 6/50* (2018.01)

(52) U.S. Cl.
USPC ..... Plt./469
CPC ..... *A01H 6/50* (2018.05)

(58) Field of Classification Search
USPC ..... Plt./469
CPC ..... A01H 5/02
See application file for complete search history.

*Primary Examiner* — Kent L Bell
(74) *Attorney, Agent, or Firm* — Penny J. Aguirre

(57) ABSTRACT

A new cultivar of *Plectranthus* plant named 'White001' that is characterized by its large white flowers with pink tones, its floriferous blooming habit, its well-branched plant habit, and its vigorous growth habit.

2 Drawing Sheets

Botanical classification: *Plectranthus* hybrid.
Variety denomination: 'White001'.

BACKGROUND OF THE INVENTION

The present invention relates to a new and distinct cultivar of *Plectranthus* of hybrid origin and will be referred to hereafter by its cultivar name, 'White001'. 'White001' is grown as a tender perennial landscape plant.

The new *Plectranthus* resulted from a breeding program conducted by the Inventors in Linbro Park, Johannesburg, South Africa. The goals of the breeding program were to develop new cultivars of *Plectranthus* with abundant, large flowers with good branching and strong and vigorous growth habits. The Inventors made crosses in March of 2015 between unnamed proprietary plants (not patented) of *Plectranthus* in the Inventors' breeding program as both the female parent and male parent. The exact parent plants are unknown as seeds were pooled from the crosses. 'White001' was selected as a single unique plant in November 2015 from the resulting seedlings of the above crosses.

Asexual propagation of the new cultivar was first accomplished by one of the Inventors by stem cuttings in December of 2015 in Linbro Park, Johannesburg, South Africa. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'White001' as a unique cultivar of *Plectranthus*.

1. 'White001' exhibits large white flowers with pink tones.
2. 'White001' exhibits a floriferous blooming habit.

3. 'White001' exhibits a well-branched plant habit.
4. 'White001' exhibits a vigorous growth habit.

'White001' can be compared to the cultivars 'Plepalila' (U.S. Plant Pat. No. 13,858) and 'De Wet F' (U.S. Plant Pat. No. 31,501). 'Plepalila' is similar to 'White001' in plant size, dense and well-branched plant habit. 'Plepalila' differs from 'White001' in having flowers that are purple in color. 'De Wet F' is similar to 'White001' in plant size, dense and well-branched plant habit. 'De Wet F' differs from 'White001' in having flowers that are purple in color.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosure includes but may not be limited to a website listing by Griffin.

BRIEF DESCRIPTION OF THE DRAWINGS

The accompanying colored photographs illustrate the overall appearance and distinct characteristics of a one year-old plant of the new *Plectranthus* as grown in a conventional greenhouse in an 18-cm container in Kaatsheuvel, The Netherlands.

The photograph in FIG. 1 provides a side view of 'White001' commencing to bloom.

Figure 1:
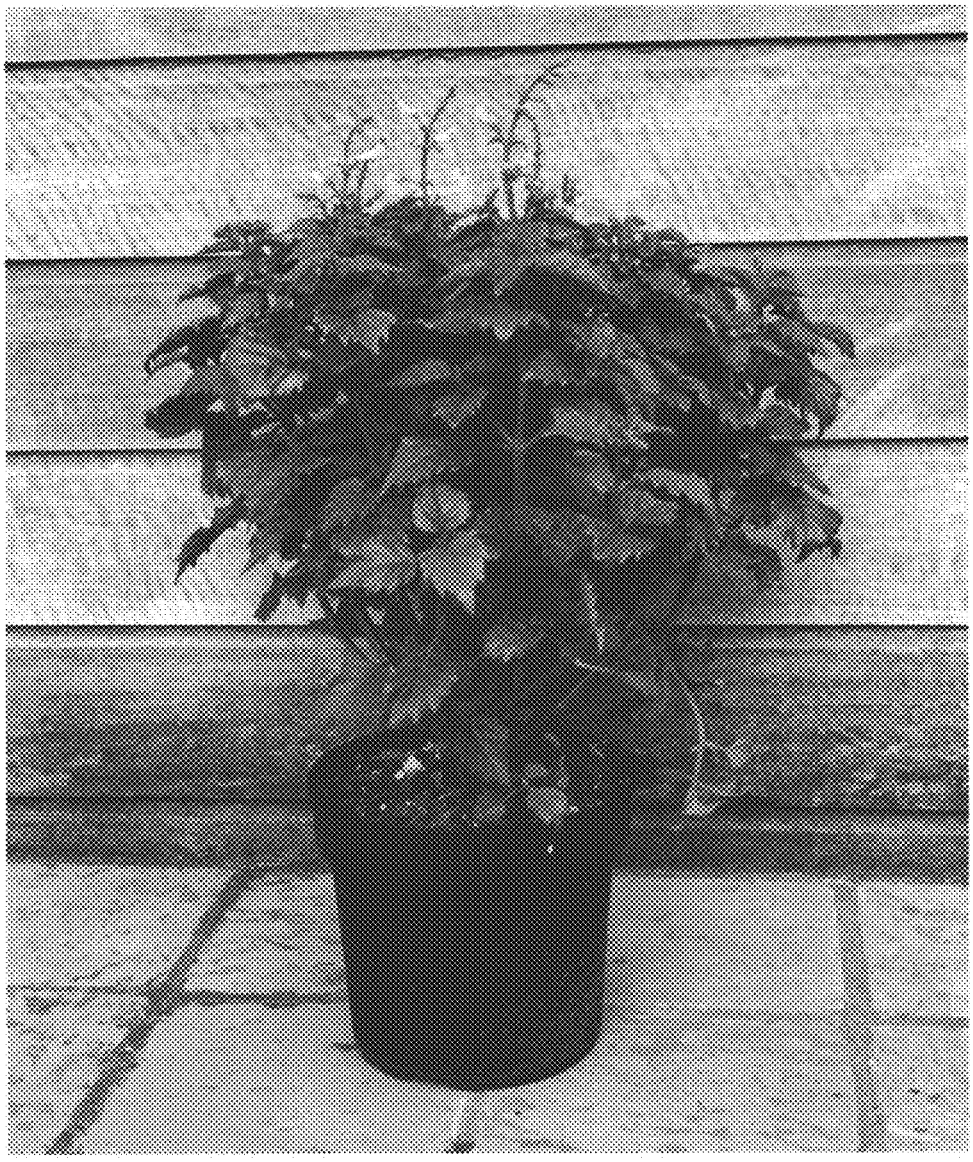
Figure 2:
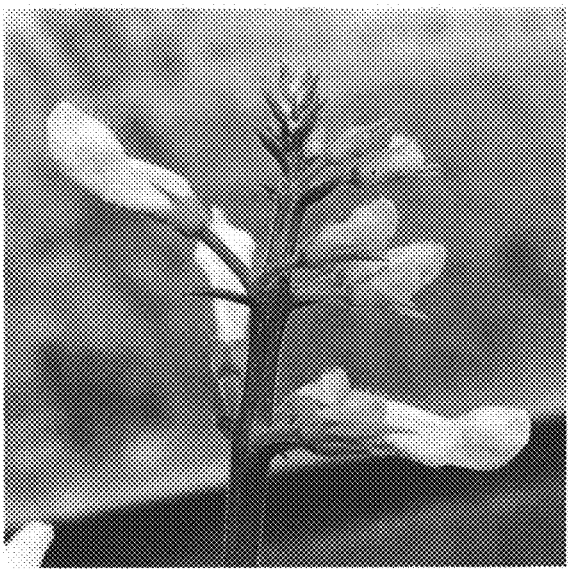

The photograph in FIG. 2 provides a close up view of the flower buds of 'White001'.

Figure 3:
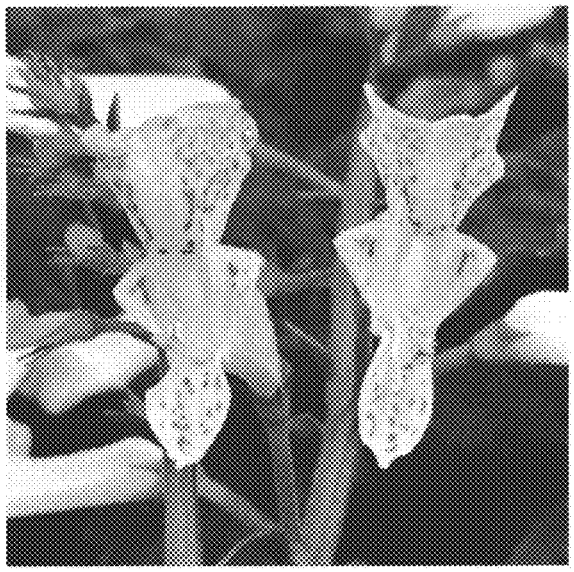

The photograph in FIG. 3. provides a close up view of the flowers of 'White001'.

Figure 4:
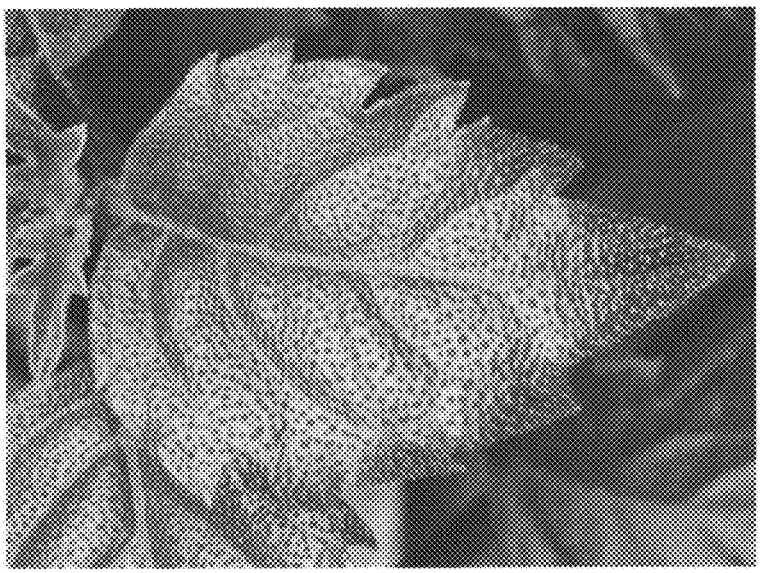

The photograph in FIG. 4. provides a close up view of the foliage of 'White001'.

The colors in the photographs are as close as possible with the digital photography techniques utilized and the color values cited in the detailed botanical description accurately describe the colors of the new *Plectranthus*.

DETAILED BOTANICAL DESCRIPTION

The following is a detailed description of one year-old plants of the new cultivar as grown in a conventional greenhouse in 18-cm containers in Kaatsheuvel, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—Blooms from mid summer to mid winter in South Africa.

*Plant type*.—Perennial, evergreen subshrub.

*Plant habit*.—Upright and well branched.

*Height and spread*.—Reaches about 42 cm in height and 46 cm in spread as a one-year old plant in a container.

*Cold hardiness*.—At least in U.S.D.A. Zone 10.

*Diseases and pests*.—No susceptibility or resistance to pests or diseases has been observed.

*Root description*.—Densely fibrous and freely branched.

*Root development*.—5 to 6 weeks to intitiate roots and an average of 5 weeks to produce a young plant from a rooted cutting.

*Propagation*.—Stem cuttings.

*Growth rate*.—Vigorous.

Stem description:

*Stem shape*.—Quadrangular.

*Stem color*.—Young; 137C, mature; 146C, tinged between 199A and 199C.

*Stem surface*.—Young stems; sparse to moderate pubescence with hairs about 1 mm in length and a color between N186A and 200A, mature; glabrous and very slightly glossy.

*Stem size*.—Lateral branches; an average of 23 cm in length and 5 mm in diameter.

*Internode length*.—Ranging between 1 cm and 8.5 cm.

*Stem strength*.—Strong.

*Stem fragrance*.—Somewhat mint-like when rubbed.

*Stem aspect*.—Upright, average angle of 40° from main branch.

*Branching*.—4 main stems and an average of 12 lateral branches per main stem.

Foliage description:

*Leaf shape*.—Ovate to broadly ovate.

*Leaf aspect*.—Slightly convex.

*Leaf division*.—Simple.

*Leaf base*.—Cuneate.

*Leaf apex*.—Acute.

*Leaf venation*.—Pinnate, upper surface 137C in color, lower surface 137C, tinged 59A.

*Leaf margins*.—Serrate.

*Leaf arrangement*.—Opposite.

*Leaf attachment*.—Petiolate.

*Leaf number*.—Average of 10 per lateral stem.

*Leaf surface*.—Upper surface; moderately glossy and moderately pubescent with soft hairs; about 1.25 mm in length and 187A in color, lower surface; slightly glossy and moderately pubescent with very short strigose soft hairs; about 0.5 mm in length and N187A in color, both surfaces slightly rugose.

*Leaf size*.—Average of 5.7 cm in length and 5 cm in width.

*Leaf color*.—Young and mature upper surface; 137A, young and mature lower surface; 137C, tinged with 59A.

*Leaf fragrance*.—Somewhat mint-like when rubbed, typical for *Plectranthus*.

*Petiole*.—An average of 2.2 cm in length and 2.5 mm in width, strong, color 146C and tinged at the top with 137C.

Inflorescence description:

*Inflorescence type*.—Axillary and terminal racemes.

*Inflorescence number*.—1 per main stem and lateral stems.

*Inflorescence fragrance*.—None.

*Lastingness of inflorescence*.—Flowers last an average of one week, self cleaning.

*Inflorescence size*.—Average of 9 cm in height and 8 cm in width.

*Flower buds*.—Average of 8 mm in length and 3 mm in diameter, oblong to slightly obovate in shape, moderately pubescent surface with very short hairs, color 145C.

*Flowers*.—Single, held outward aspect, labiate in form, average of 2.8 cm in length (depth), 2.4 cm in in height (vertical) and 1.5 cm in diameter (horizontal) with throat diameter 2 mm in width, tube portion; 1.8 cm in length and 4 mm in diameter at widest part, average of 26 flowers per inflorescence.

*Petals*.—5; base fused into tube, 2 petals fused into one upper petal lobe, two lateral petal lobes and one lower petal lobe, upper petal lobe 1 cm in length and 1.1 cm in width, upper petal obcordate in shape, lateral petal reniform in shape, lower petal orbicular in shape, folded, margins entire, color; when opening and fully open upper surface N155B with spots 72B, when opening and fully open lower surface, throat and tube N155B, both surfaces matte and smooth.

*Calyx*.—5 mm in length and 3 mm in width, comprised of 5 sepals (2 lower, 2 lateral, 1 upper); rotate and fused at base, lower sepals; 5 mm in length, 1 mm in width, linear in shape, narrowly acute apex, entire margins, lateral sepals; 4 mm in length, 1 mm in width, linear in shape, narrowly acute apex, entire margins, upper sepal; 2 mm in length, 2.5 mm in width, ovate in shape, acute apex, entire margins, all surfaces are smooth, matte, glabrous, moderately pubescent, all surfaces when opening and mature 137C on color.

*Peduncles*.—Moderately strong, average of 8 cm in length and 3 mm in diameter, held at an angle of 0° to vertical for terminal inflorescence and 45° for axillary inflorescences, slightly glossy surface, 137C in color, surface slightly glossy and moderately to densely covered with very short glandular hairs.

*Pedicels*.—Moderately strong, average of 8 mm in length and 1 mm in diameter, held at a 40° angle to peduncle, 137C in color, surface matte and moderately covered with very short glandular hairs; 0.3 mm in length and a color between N186C and 200A.

Reproductive organs:

*Pistils*.—1, pistil; 2.5 mm in length and 1 mm in diameter, stigma; 1 mm in diameter, cleft-shaped and 85B in color, style; 2 cm in length, N155A, ovary; N155A in color.

*Stamens*.—4, anthers; dorsifixed, short oblong in shape, average of 1 mm in length and 0.5 mm in width, N77A in color, filament; 6 mm in length, N155A in color, pollen; low in quantity, 155A in color.

*Fruit and seeds*.—No fruit or seed development has been observed.

It is claimed:

1. A new and distinct cultivar of *Plectranthus* plant named 'White001' as herein illustrated and described.

* * * * *